US008435194B2

(12) United States Patent
Dverin et al.

(10) Patent No.: US 8,435,194 B2
(45) Date of Patent: May 7, 2013

(54) DEVICE FOR RF HEATING AND MECHANICAL MASSAGE OF BIOLOGICAL TISSUE

(75) Inventors: Alexander Dverin, Netanya (IL); Yevgeny Pens, Haifa (IL); Ziv Karni, Kfar Shmaryahu (IL); Ziv Shabat, Kibbutz Givat Haim Meuchad (IL); Alexander Britva, Migdal Haemek (IL)

(73) Assignee: Alma Lasers Ltd, Caesarea (IL)

( * ) Notice: Subject to any disclaimer, the term of this patent is extended or adjusted under 35 U.S.C. 154(b) by 268 days.

(21) Appl. No.: 12/834,033

(22) Filed: Jul. 12, 2010

(65) Prior Publication Data

US 2011/0009783 A1   Jan. 13, 2011

Related U.S. Application Data

(60) Provisional application No. 61/224,883, filed on Jul. 12, 2009.

(51) Int. Cl.
*A61H 15/00* (2006.01)
(52) U.S. Cl.
USPC .......................................... 601/112; 601/113
(58) Field of Classification Search ................ 601/7, 10, 601/15, DIG. 1, DIG. 4, DIG. 5, 46, 123, 601/126, 134, 112, 113; 607/101, 115
See application file for complete search history.

(56) References Cited

U.S. PATENT DOCUMENTS

| 4,858,600 | A | 8/1989 | Gross et al. | |
| 6,438,424 | B1 | 8/2002 | Knowlton | |
| 6,662,054 | B2 | 12/2003 | Kreindel | |
| 6,673,096 | B2 | 1/2004 | Lach | |
| 7,630,774 | B2 | 12/2009 | Karni | |
| 7,762,964 | B2 * | 7/2010 | Slatkine | ............................ 601/7 |
| 2007/0173749 | A1 * | 7/2007 | Williams et al. | .............. 601/123 |
| 2008/0183252 | A1 * | 7/2008 | Khen | ............................ 607/101 |
| 2008/0200778 | A1 * | 8/2008 | Taskinen et al. | .............. 600/306 |
| 2009/0171424 | A1 | 7/2009 | Britva | |

FOREIGN PATENT DOCUMENTS

WO        WO98/05286        2/1998

* cited by examiner

*Primary Examiner* — Michael A. Brown
(74) *Attorney, Agent, or Firm* — Mark M. Friedman

(57) ABSTRACT

A skin treatment device combines an RF treatment arrangement with a mechanical massage arrangement, preferably with the massage device in the form of an annular massage head encircling and rotating around the RF applicator. Also disclosed are configurations with a liquid dispenser for delivering a liquid to the skin under the device. According to one option, the skin contact surface of the RF applicator itself is provided in part by a rolling ball liquid applicator.

23 Claims, 6 Drawing Sheets

DEVICE FOR RF HEATING AND MECHANICAL MASSAGE OF BIOLOGICAL TISSUE

FIELD AND BACKGROUND OF THE INVENTION

The present invention relates to apparatus and methods for heating biological tissue using radio frequency (RF) electromagnetic waves.

It is known to employ electromagnetic energy for delivering energy into biological tissue. Of most relevance to the present invention are devices which perform thermal treatment of the skin by delivery of RF energy. Examples believed to be representative of the current state of the art for such devices, the contents of which are hereby incorporated by reference, include: U.S. Pat. No. 7,630,774, US20090171424 and U.S. Pat. No. 6,662,054.

In the field of massage devices, it is known to employ spherical bodies mounted in a rotating structure to provide a mechanical massage effect. An example of such a device may be found in U.S. Pat. No. 4,858,600, which is hereby incorporated by reference.

SUMMARY OF THE INVENTION

We now disclose that when RF energy is applied to treat biological tissue (for example, skin), it is useful to apply mechanical massage to the tissue in full or partial synchrony with the RF treatment.

In some embodiments, this is carried out using a device including a handpiece including: (i) an RF applicator; and (ii) a "ring-shaped" massager which surrounds the RF applicator.

Although not a limitation, in some embodiments, this is carried out using RF energy provided by any teaching or combination of teachings disclosed in U.S. Pat. No. 7,630,774.

Mechanical massage of skin is known to affect dermal and subcutaneous connective tissue, promoting blood flow, relieving sore muscles and tension, and stimulating the release of harmful toxins in the skin. Mechanical massage enhances microcirculation and facilitates drainage of trapped intercellular fluid to the lymphatic system and may act to form a callus of thicker more hydrated subcutaneous tissue that has a smoother contour due to fewer local depressions.

RF energy is known to affect the same regions of the skin, progressively increasing heat-inducing thermal effects and local metabolism. RF energy (for example, RF energy delivered in accordance with one or more teachings of U.S. Pat. No. 7,630,774, or using a device operating according to one or more teachings of U.S. Pat. No. 7,630,774) and mechanical massage applied in near, partial, or full conjunction achieve a synergy, non-limiting examples of which include improved temporary reduction in the appearance of cellulite, remodeling of collagen, and alleviation of wrinkles.

In a non-limiting scenario, the device of the present invention is used as follows: (i) an RF applicator is placed in contact with the skin surface; (ii) RF power is delivered from the applicator to the skin, thereby heating underlying tissue layers; (iii) at least partially concomitant with the delivery of RF-power, a massage applicator is applied to the skin, for example a rotating ring of balls arranged around the RF applicator, thereby massaging the underlying tissue layers.

In a non-limiting example, we contemplate modifying a system for skin treatment having an RF subsystem, similar to that disclosed in U.S. Pat. No. 7,630,774, to include a massage subsystem configured to mechanically massage the skin under treatment and/or adjacent skin.

In one example, this modification is carried out so that a given location on the skin is: (i) first subjected to massage; (ii) then subjected to RF energy; and (iii) once again, subjected to massage.

Thus, according to an embodiment of the present invention there is provided, a skin treatment device comprising: (a) an RF treatment arrangement comprising: (i) an RF applicator terminating in a skin contact surface through which RF energy is delivered into the skin, and (ii) an RF energy source capable of directing an RF power signal to the applicator; and (b) a mechanical massage arrangement comprising: (i) a massage manipulator comprising at least one massage head, the massage manipulator defining a skin contact region, and (ii) a motor, mechanically linked in driving relation to the at least one massage head so as to displace the at least one massage head relative to a skin surface, wherein the skin contact region substantially encircles the RF applicator such that, when the device is brought in contact with the skin and the RF treatment arrangement and the mechanical massage arrangement are actuated, mechanical massage is performed on a region of skin adjacent to, or overlapping with, a region treated by the RF energy.

According to an embodiment of the present invention, the at least one massage head is an annular massage head deployed so as to encircle the RF applicator.

According to an embodiment of the present invention, the annular massage head includes a plurality of rolling elements deployed to provide rolling engagement with the skin surface.

According to an embodiment of the present invention, the annular massage head includes a plurality of spherical elements deployed to provide rolling engagement with the skin surface.

According to an embodiment of the present invention, the annular massage head is rotatably mounted so as to rotate about an axis, and wherein the axis substantially coincides with a central axis of the RF applicator.

According to an embodiment of the present invention, the annular massage head is interconnected so as to rotate together with a gear wheel, and wherein the gear wheel has a central opening, at least part of the RF treatment arrangement extending through the central opening.

According to an embodiment of the present invention, the motor and the RF energy source are deployed within a common housing, and wherein the motor is provided with electrical shielding.

According to an embodiment of the present invention, the motor and the RF energy source are deployed within a common housing, the device further comprising a liquid dispenser deployed at least partially within the housing and configured to deliver a liquid to a region of skin underlying the device.

According to an embodiment of the present invention, the liquid dispenser defines a flow path in thermal contact with at least part of the RF applicator.

According to an embodiment of the present invention, there is also provided a cooling arrangement deployed within the housing and configured to cool the liquid, thereby cooling the RF applicator.

According to an embodiment of the present invention, the liquid dispenser defines a flow path passing through at least part of the RF applicator.

According to an embodiment of the present invention, the flow path extends to deliver the liquid at the skin contact surface of the RF applicator.

According to an embodiment of the present invention, the flow path terminates at a rolling ball liquid applicator formed as part of the RF applicator so as to provide at least part of the skin contact surface of the RF applicator.

According to an embodiment of the present invention, the liquid dispenser defines a flow path extending through the massage manipulator so as to deliver the liquid via the at least one massage head.

According to an embodiment of the present invention, the massage head includes a plurality of spherical elements deployed to provide rolling engagement with the skin surface, and wherein the flow path delivers the liquid to a surface of at least one of the spherical elements for rolling application to the skin surface.

There is also provided according to an embodiment of the present invention, a skin treatment device comprising: (a) a housing; (b) an RF treatment arrangement deployed at least partially within the housing, the RF treatment arrangement comprising: (i) an RF applicator terminating in a skin contact surface through which RF energy is delivered into the skin, and (ii) an RF energy source capable of directing an RF power signal to the applicator; and (c) a liquid dispenser deployed at least partially within the housing and configured to deliver a liquid to a region of skin underlying the RF applicator.

According to an embodiment of the present invention, the liquid dispenser defines a flow path in thermal contact with at least part of the RF applicator.

According to an embodiment of the present invention, there is also provided a cooling arrangement deployed within the housing and configured to cool the liquid, thereby cooling the RF applicator.

According to an embodiment of the present invention, the liquid dispenser defines a flow path passing through at least part of the RF applicator.

According to an embodiment of the present invention, the flow path terminates at a rolling ball liquid applicator formed as part of the RF applicator so as to provide at least part of the skin contact surface of the RF applicator.

According to an embodiment of the present invention, there is also provided a mechanical massage arrangement comprising: (a) a massage manipulator comprising at least one massage head, the massage manipulator defining a skin contact region, and (b) a motor, mechanically linked in driving relation to the at least one massage head so as to displace the at least one massage head relative to a skin surface, wherein the skin contact region substantially encircles the RF applicator such that, when the device is brought in contact with the skin and the RF treatment arrangement and the mechanical massage arrangement are actuated, mechanical massage is performed on a region of skin adjacent to, or overlapping with, a region treated by the RF energy.

According to an embodiment of the present invention, the at least one massage head is an annular massage head deployed so as to encircle the RF applicator.

According to an embodiment of the present invention, the annular massage head includes a plurality of spherical elements deployed to provide rolling engagement with the skin surface.

According to an embodiment of the present invention, the liquid dispenser defines a flow path extending through the massage manipulator so as to deliver the liquid to a surface of at least one of the spherical elements for rolling application to the skin surface.

According to an embodiment of the present invention, the annular massage head is rotatably mounted so as to rotate about an axis, and wherein the axis substantially coincides with a central axis of the RF applicator.

BRIEF DESCRIPTION OF THE DRAWINGS

The invention is herein described, by way of example only, with reference to the accompanying drawings, wherein.

While the invention is described herein by way of example for several embodiments and illustrative drawings, those skilled in the art will recognize that the invention is not limited to the embodiments or drawings described. It should be understood that the drawings and detailed description thereto are not intended to limit the invention to the particular form disclosed, but on the contrary, the invention is to cover all modifications, equivalents and alternatives falling within the scope of the present invention as defined by the appended claims.

DESCRIPTION OF THE PREFERRED EMBODIMENTS

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice.

Figure 1:
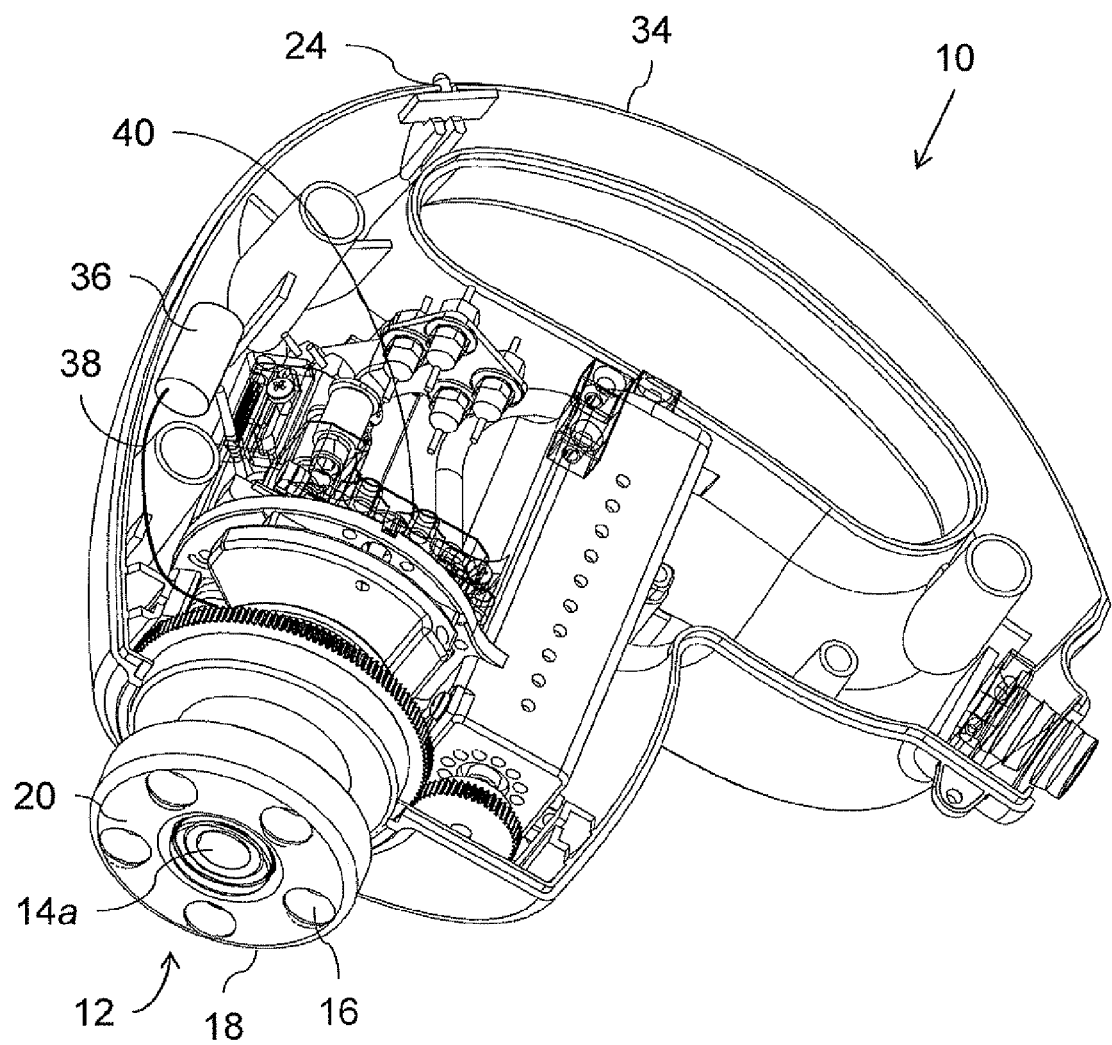
FIG. 1 is an isometric view of a handpiece for treating skin with RF power and mechanical massage, according to some embodiments of the present invention, the device being shown with a front part of a housing removed.
Figure 2:
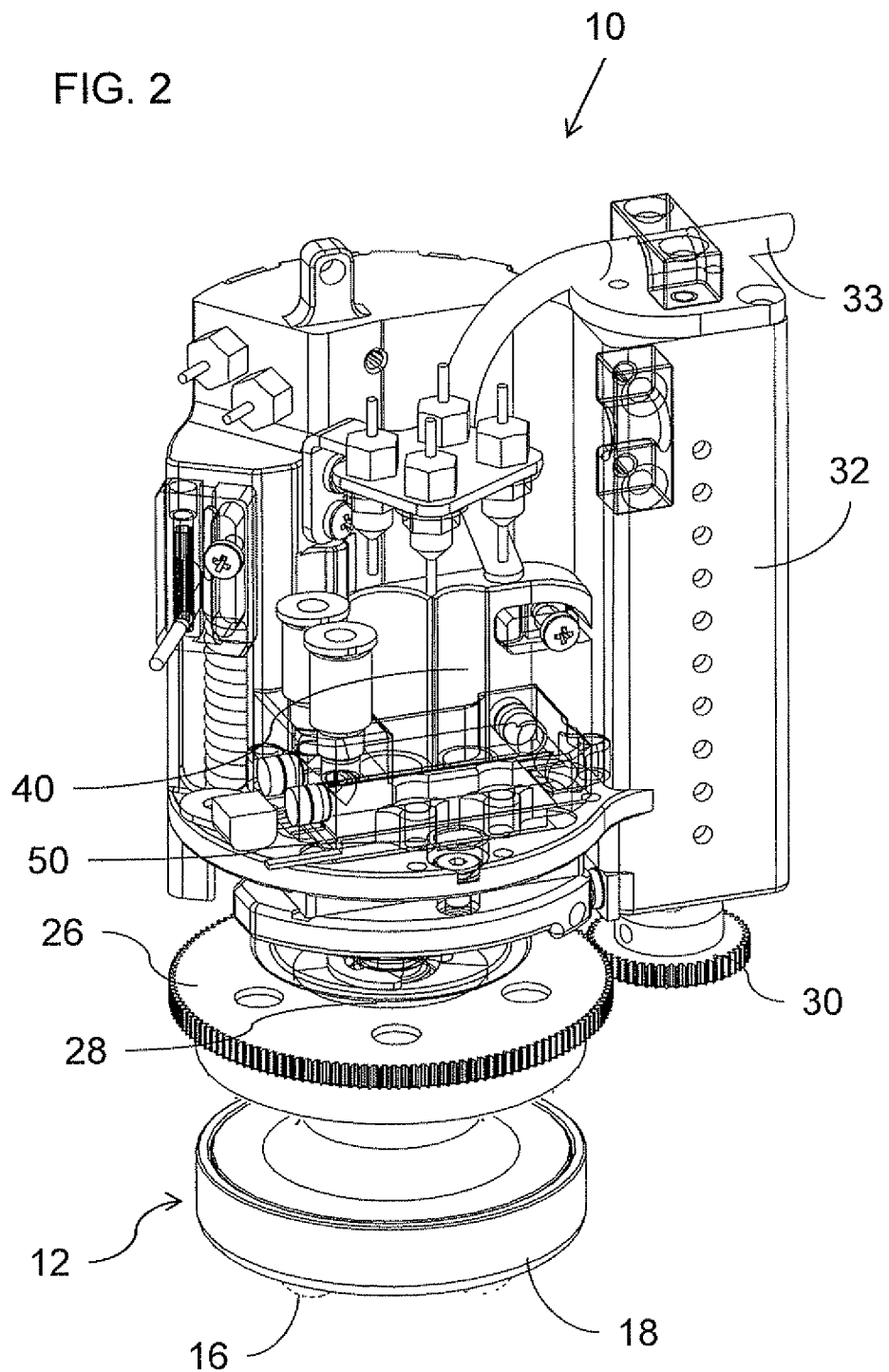
FIG. 2 is an isometric view of components of the handpiece of FIG. 1.
Figure 3:
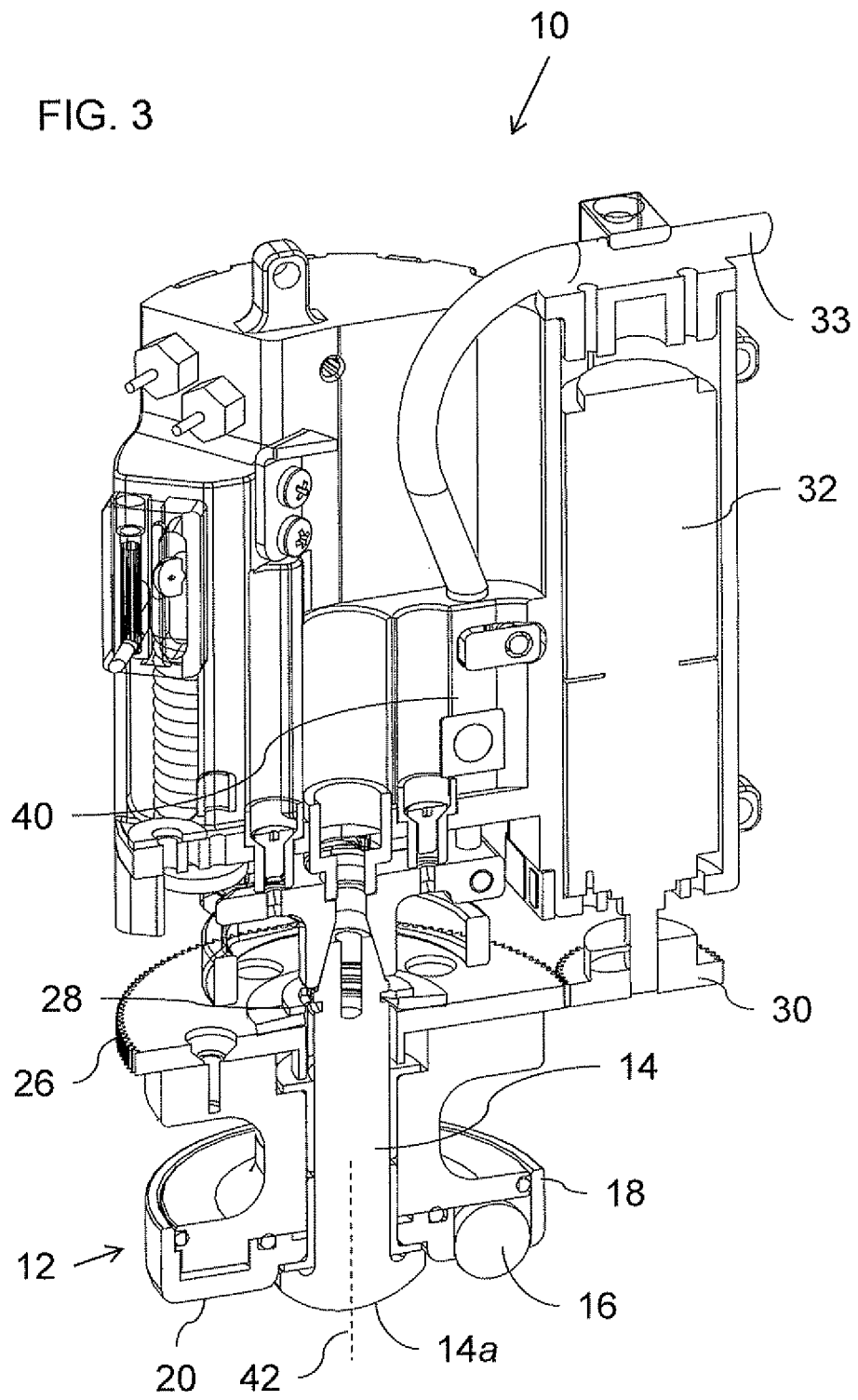
FIG. 3 is a cut-away view of the components of FIG. 2.
Figure 4:
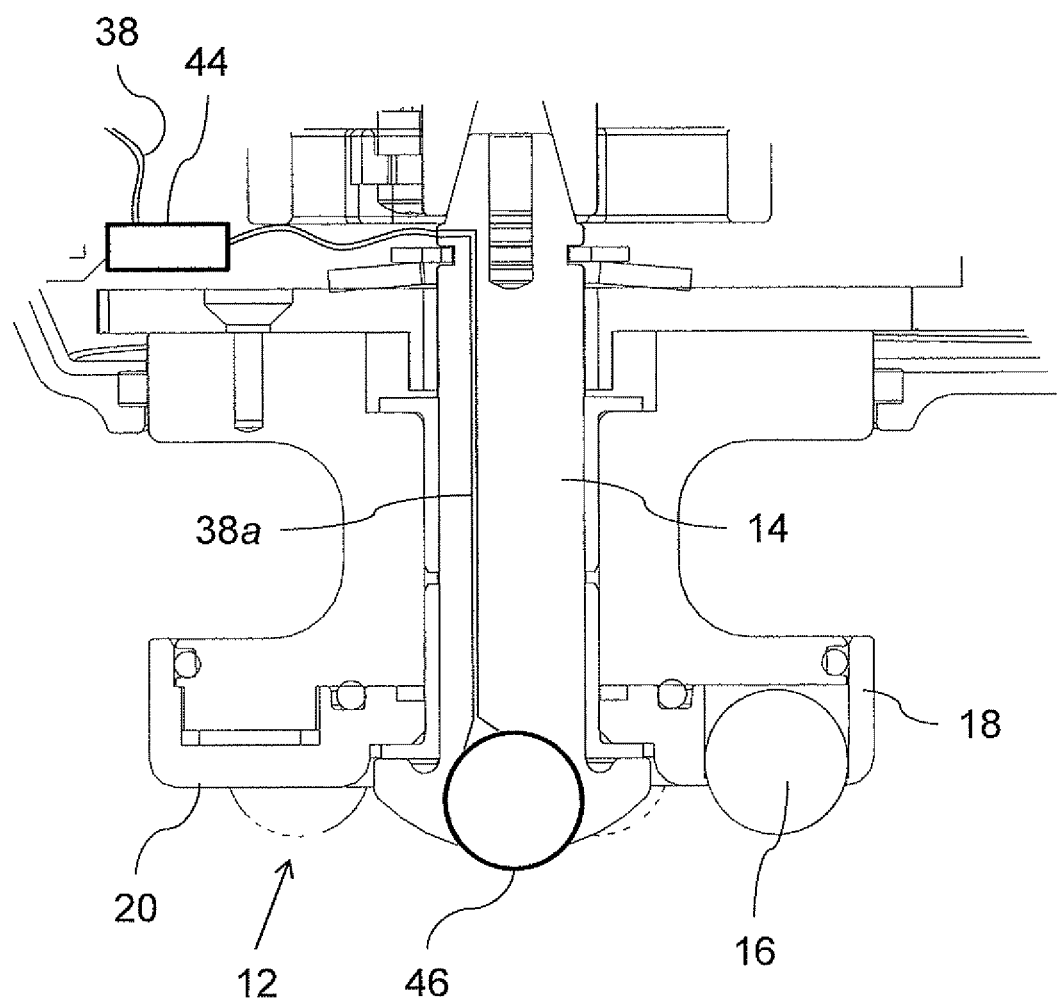
FIG. 4 is an enlarged partial cross-sectional view of a portion of the handpiece of FIG. 1 illustrating a first implementation of a liquid dispensing flow path.
Figure 5:
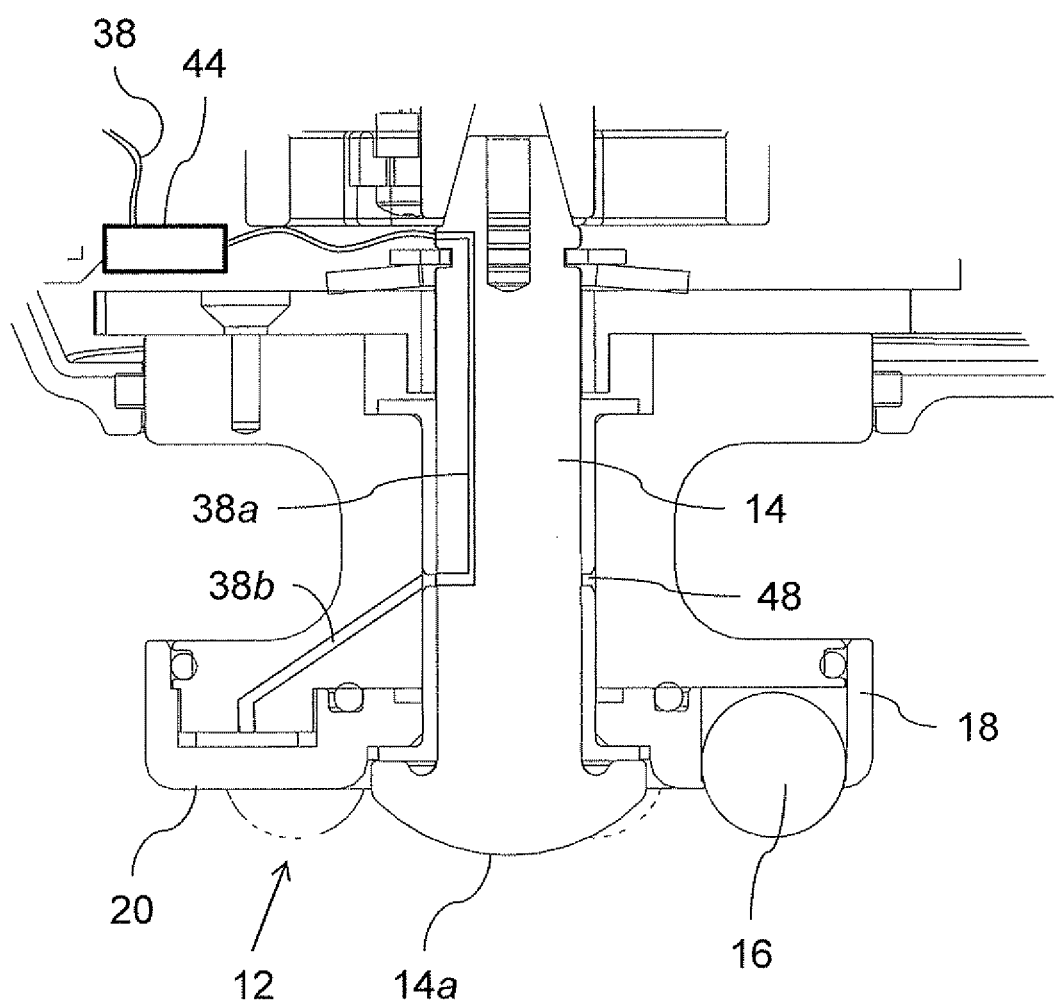
FIG. 5 is an enlarged partial cross-sectional view of a portion of the handpiece of FIG. 1 illustrating a second implementation of a liquid dispensing flow path.
Figure 6:
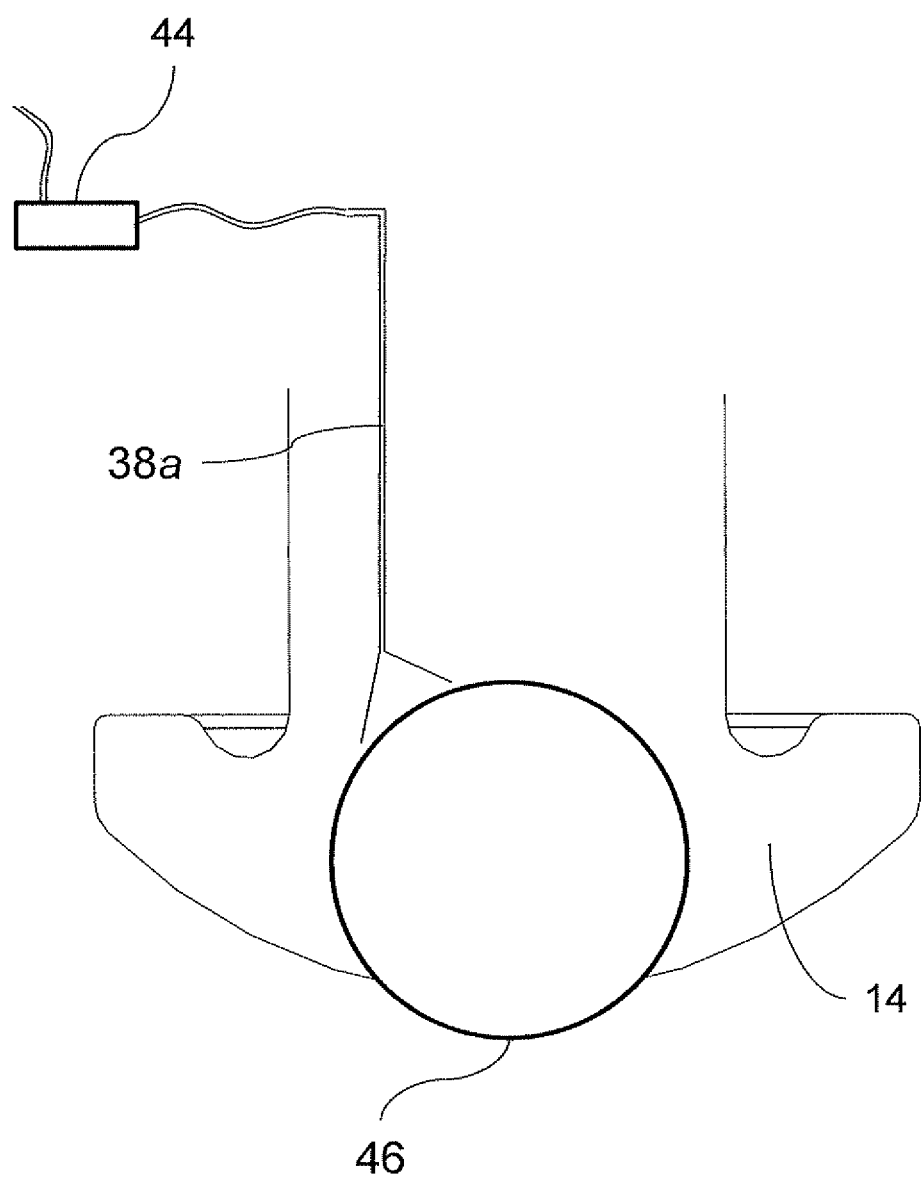
FIG. 6 is an enlarged partial cross-sectional view of a portion of a handpiece according to an alternative embodiment of the present invention.

By way of introduction, the present invention has a number of different aspects, each of which is believed to be of individual importance, but which may be used together in particular synergy. A first aspect of the invention relates to a combination skin treatment device which performs simultaneous mechanical massage and RF energy treatment. A second aspect of the invention relates to a device which delivers a liquid (cream, gel, ointment, paste or other fluid substance) to the skin contact surface of a skin treatment device with RF energy treatment. FIGS. 1-5 relate to an illustrative embodiment in which both of these aspects are combined in synergy, while FIG. 6 presents an alternative embodiment in which the liquid delivery aspect is implemented without mechanical massage.

Combination RF Energy and Mechanical Massage

Turning now to the drawings, FIGS. 1-5 illustrate a skin treatment device, preferably implemented as a "handpiece" 10, in accordance with some embodiments of the present invention, that is intended for integration in a system for skin treatment. The system for skin treatment includes an RF energy subsystem terminating in an RF applicator 14 and a massage subsystem terminating in a massage applicator 12.

In more detail, the RF energy subsystem (also referred to as an "RF treatment arrangement") includes RF applicator 14 terminating in a skin contact surface 14a through which RF energy is delivered into the skin, and an RF energy source 40 configured to direct an RF power signal to applicator 14.

RF skin treatment systems per se are well developed, and are readily commercially available. Examples of commercially available RF treatment systems which could readily be modified according to the teachings of the present invention include Accent XL system available from ALMA Lasers Ltd. (Israel), and Velashape and Velasmooth available from SYNERON Ltd. (Israel). For conciseness of this disclosure, features of the RF treatment subsystem that are not new will not be described here.

By way of a non-limiting but particularly preferred implementation, the RF energy subsystem may be implemented as described in U.S. Pat. No. 7,630,774, which is hereby incorporated by reference in its entirety. In this case, substantially the entire skin contact surface 14a of the RF applicator 14 serves as a single electrode for delivering the RF energy into the skin. It should be noted however that systems with two or more electrodes may also be used to implement the present invention. In certain cases, skin contact surface 14a may be split into two concentric electrode regions.

RE applicator 14 is typically roughly symmetrical about a central axis 42 that, when extrapolated, also corresponds roughly to the center of the RF treatment region for the current position of the device.

Turning now to the massage subsystem (also referred to as a "mechanical massage arrangement"), massage applicator 12 is preferably implemented as a massage manipulator with at least one massage head. In this context, the term "massage head" refers to a moving body with features, or rolling sub-elements, which perform a massage function as is moves in contact with the skin. The one or more massage heads define a skin contact region of the massage manipulator, i.e., the region of the skin that will be treated with massage by operation of the massage heads while the device is maintained in a given position in contact with the skin. A motor 32 is mechanically linked in driving relation to the at least one massage head so as to displace the at least one massage head relative to a skin surface.

It is a particular feature of certain embodiments of the present invention that the skin contact region substantially encircles the RF applicator such that, when device 10 is brought in contact with the skin and the RF treatment arrangement and the mechanical massage arrangement are actuated, mechanical massage is performed on a region of skin adjacent to, or overlapping with, a region treated by the RF energy. It should be mentioned that the device is particularly suited to in-motion treatment where the handpiece is drawn across the skin surface during use. This typically results in a treatment sequence in which the skin passing under the device is massaged, then heated and then massaged again.

In a particularly preferred implementation as illustrated here, massage applicator 12 is implemented as a single annular massage head (or "ring") 18 deployed so as to encircle part of RF applicator 14, and is rotatably mounted so as to rotate about an axis, that may be substantially coinciding with the central axis 42 of the RF applicator. The annular massage head preferably includes a plurality of rolling elements, most preferably spherical elements (balls) 16, deployed to provide rolling engagement with the skin surface.

The balls 16 are preferably retained by a face plate 20 of the massage head which has openings through which balls 16 project. The various parts of massage head 18 and balls 16 may be made from any suitable material, preferably chosen so as to avoid interactions with the RF energy near RF applicator 14. A non-limiting example of a suitable material is an insulating, biocompatible, lightweight, low-friction, and wear-resistant thermoplastic such as polyoxymethylene (marketed as DELRIN® by the E.I. du Pont de Nemours and Company of DE, USA.), or other plastics, ceramics or the like. Non-limiting exemplary dimensions for the massage subsystem are: a 50 mm diameter of ring 18, a 10 mm diameter of ball 16, and a ring 18 rotation speed of 150 rpm. Optionally, it may be advantageous to operate the massage head at a rate of rotation which is synchronized with a pulse width modulation (PWM) frequency of the RF treatment, for example, at the same frequency, or where one is an integer multiple of the other.

Massage head 12 is rotated by motor 32 by engagement of a drive gear 30 of motor 32 with a gear wheel 26 interconnected so as to rotate together with ring 18. Gear wheel 26 as shown here is mounted on a bearing 28 located at a central opening of the gear wheel through which at least part of the RF treatment arrangement extends.

Power for motor 32 and RF energy for the RF applicator 14 are supplied via supply tube 33. When motor 32 is powered, it turns drive gear 30, which turns gear 26, turning ring 18 and balls 16, which massage an annular area of skin around the area in contact with the RF applicator 14.

Electric motor 32 and RF source 40 are preferably housed in a common housing 34. Electric motor 32 is preferably provided with electrical shielding in order to minimize RE interference on the massage subsystem. Motor 32 may be a readily commercially available shielded DC brushless motor. For safety, motor 32 can be operable to detect changes in resistance to rotation of ring 18, to adjust its input current to compensate for such changes in resistance, and to interrupt its input current if resistance exceeds a defined threshold.

RF applicator 14 and massage applicator 12 are preferably arranged such that when the handpiece 10 is positioned for treating an area of a subject's skin, each applicator is in contact with the skin. During treatment, the skin treatment system supplies RF energy through RF applicator 14 to the skin and mechanical force through massage applicator 12 to the skin.

The massage applicator 12 and the RE applicator 14 can be activated separately or simultaneously. In one non-limiting scenario, the massage applicator 12 is operated continuously while the device is in use, and the RE energy is selectively actuated by an operator actuating a button or trigger 24 on the device. Typically, the applicators are activated simultaneously as handpiece 10 is moved over the skin surface, for example, in circular motion, across a desired treatment area, for example, a rectangular area, until RF applicator 14 has applied a predetermined amount of energy to the treatment area.

In a non-limiting example, a 450 square cm treatment area of a subject's posterior thigh is treated by RE applicator 14 supplied with 120 W to 160 W at 40.68 MHz until 60 kJ to 100 kJ of total energy have been emitted. Concurrently massage applicator 12 is rotated at 150 revolutions per minute, massaging the skin.

The arrangement of massage applicator 12 annularly around RF applicator 14 ensures that no matter which direction handpiece 10 is moved, skin passes under massage applicator 12 immediately before and after it passes under RF applicator 14, contributing to the effective synergy of the two applications. Furthermore, without in any way limiting the scope of the present invention, in certain preferred implementations where a continuous-rotation massage motion used, it is believed that this motion is particularly effective at inducing a net flow of body fluids in the region undergoing massage, thereby effectively mobilizing body fluids and enhancing uniformity of the RF treatment.

In some embodiments, handpiece 10 further comprises a skin detector operative to detect physical characteristics of the skin in contact with massage applicator 16 and a control circuit operative to alter the ring rotation speed according to input from the skin detector.

In some embodiments, handpiece 10 comprises a velocity detector operative to detect the handpiece velocity and a control circuit operative to alter the ring 18 rotation speed according to input from the velocity detector.

Combination RF Energy and Liquid Dispensing

Turning now to a second aspect of the present invention, this relates to dispensing of a liquid to the skin contact surface of a skin treatment device which performs RF energy treatment. As mentioned above, this feature may be used to advantage in synergy with the RF-and-massage combination described above. Accordingly, this aspect of the invention will be described primarily with reference to FIGS. 1-5 in a combined embodiment. Thereafter, brief reference will be made to FIG. 6 which relates to an implementation of this second aspect of the invention without a massage applicator.

Referring now again to FIG. 1, according to an embodiment of the invention, the device includes a liquid dispenser 36 deployed at least partially within housing 34 and configured to deliver a liquid along a flow path 38 to a region of skin underlying the device, i.e., within the outer perimeter of the skin contact region of massage applicator 12, whether actually in the skin contact region of the massage system or the skin contact region of the RF applicator, or therebetween.

Although not limited to any particular liquid, this aspect of the present invention is believed to be of particular advantage when implemented using oil. Specifically, the oil serves to lubricate contact between the RF applicator and/or massage applicator against the skin, and may help to disperse heat at the skin surface, rendering the treatment more uniform. Optionally, mineral oil or other oils or lotions providing a soothing effect and/or other beneficial effects to the skin may be used.

In certain preferred implementations of the RF subsystem, a cooling arrangement, typically employing thermoelectric coolers (TEC) 50 (FIG. 2), is deployed to cool RF applicator 14 to below body temperature. According to an optional feature of the present invention, a part of flow path 38 (denoted 38*a*) is deployed in thermal contact with at least part of the RF applicator. Flow path 38*a* may pass adjacent to the outside surface of RF applicator 14, or as shown in the examples of FIGS. 4 and 5, may pass within RF applicator 14. A cooling arrangement 44 (preferably TEC-based) is deployed within housing 34 so as to cool the liquid. The liquid flowing through flow path 38*a* then contributes to the overall cooling of RF applicator 14.

FIG. 4 illustrates one particularly preferred option for implementing flow path 38*a* according to which the flow path extends to deliver the liquid at the skin contact surface of the RF applicator. In the example illustrated here, the flow path terminates at a rolling ball liquid applicator formed as part of the RF applicator so as to provide at least part of a skin contact surface of the RF applicator. This ensures that the liquid is dispensed exactly at the skin contact surface of RF applicator 14.

The rolling ball liquid applicator is typically implemented using one or more balls 46 retained within, but projecting from, the tip of the RF applicator. By way of one non-limiting example, as with the main body of RF applicator 14, ball 46 may be formed from aluminum coated with aluminum oxide or some other insulating material such as Teflon or other plastics. Alternatively, other non-magnetic metals, such as copper, stainless steel, brass, bronze, and beryllium brass, may be used. An insulating coating is desirable for decreasing the likelihood of spark generation, and for homogenization of the RF current distribution.

Turning now to FIG. 5, this shows an alternative implementation in which a part of flow path 38, designated 38*b*, extends through rotating massage applicator 12 to dispense the liquid via the rotating balls 16 of the massage device. Connection between the non-rotating flow path 38*a* and the rotating part of the flow path 38*b* may be achieved at an annular manifold 48 extending around the periphery of RF applicator 14.

Turning finally to FIG. 6, as mentioned earlier, the liquid dispensing aspect of the present invention may also be used to advantage in an RF energy skin treatment device which does not include a massage subsystem. FIG. 6 illustrates schematically the terminal portion of the RF applicator 14 of such an implementation. The structure and function of the device shown is fully analogous to that of FIG. 4 described above, with similar components being labeled similarly, and need not be described again.

It will be appreciated that the above descriptions are intended only to serve as examples, and that many other embodiments are possible within the scope of the present invention as defined in the appended claims.

What is claimed is:

1. A skin treatment device comprising:
   (a) an RF treatment arrangement comprising:
      (i) an RF applicator terminating in a skin contact surface through which RF energy is delivered into the skin, and
      (ii) an RF energy source capable of directing an RF power signal to said applicator; and
   (b) a mechanical massage arrangement comprising:
      (i) a massage manipulator comprising at least one annular massage head deployed so as to encircle said RF applicator, said massage manipulator defining a skin contact region, and
      (ii) a motor, mechanically linked in driving relation to said at least one massage head so as to displace said at least one massage head relative to a skin surface,
   wherein said skin contact region substantially encircles said RF applicator such that, when the device is brought in contact with the skin and said RF treatment arrangement and said mechanical massage arrangement are actuated, mechanical massage is performed on a region of skin adjacent to, or overlapping with, a region treated by the RF energy,
and wherein said annular massage head is rotatably mounted so as to rotate about an axis, and wherein said axis substantially coincides with a central axis of said RF applicator.

2. The skin treatment device of claim 1, wherein said annular massage head is interconnected so as to rotate together with a gear wheel, and wherein said gear wheel has a central opening, at least part of said RF treatment arrangement extending through said central opening.

3. The skin treatment device of claim 1, wherein said motor and said RF energy source are deployed within a common housing, and wherein said motor is provided with electrical shielding.

4. A skin treatment device comprising:
   (a) an RF treatment arrangement comprising:
      (i) an RF applicator terminating in a skin contact surface through which RF energy is delivered into the skin, and (ii) an RF energy source capable of directing an RF power signal to said applicator; and
(b) a mechanical massage arrangement comprising:
(i) a massage manipulator comprising at least one annular massage head deployed so as to encircle said RF applicator, said annular massage head including a plurality of rolling elements deployed to provide rolling engagement with the skin surface, said massage manipulator defining a skin contact region, and
(ii) a motor, mechanically linked in driving relation to said at least one massage head so as to displace said at least one massage head relative to a skin surface,
wherein said skin contact region substantially encircles said RF applicator such that, when the device is brought in contact with the skin and said RF treatment arrangement and said mechanical massage arrangement are actuated, mechanical massage is performed on a region of skin adjacent to, or overlapping with, a region treated by the RF energy.

5. The skin treatment device of claim 4, wherein said plurality of rolling elements are implemented as a plurality of spherical elements deployed to provide rolling engagement with the skin surface.

6. A skin treatment device comprising:
(a) an RF treatment arrangement comprising:
(i) an RF applicator terminating in a skin contact surface through which RF energy is delivered into the skin, and
(ii) an RF energy source capable of directing an RF power signal to said applicator; and
(b) a mechanical massage arrangement comprising:
(i) a massage manipulator comprising at least one annular massage head deployed so as to encircle said RF applicator, said massage manipulator defining a skin contact region, and
(ii) a motor, mechanically linked in driving relation to said at least one massage head so as to displace said at least one massage head relative to a skin surface,
wherein said skin contact region substantially encircles said RF applicator such that, when the device is brought in contact with the skin and said RF treatment arrangement and said mechanical massage arrangement are actuated, mechanical massage is performed on a region of skin adjacent to, or overlapping with, a region treated by the RF energy,
and wherein said motor and said RF energy source are deployed within a common housing, the device further comprising a liquid dispenser deployed at least partially within said housing and configured to deliver a liquid to a region of skin underlying the device.

7. The skin treatment device of claim 6, wherein said liquid dispenser defines a flow path in thermal contact with at least part of said RF applicator.

8. The skin treatment device of claim 7, further comprising a cooling arrangement deployed within said housing and configured to cool the liquid, thereby cooling said RF applicator.

9. The skin treatment device of claim 6, wherein said liquid dispenser defines a flow path passing through at least part of said RF applicator.

10. The skin treatment device of claim 9, wherein said flow path extends to deliver the liquid at the skin contact surface of said RF applicator.

11. The skin treatment device of claim 9, wherein said flow path terminates at a rolling ball liquid applicator formed as part of said RF applicator so as to provide at least part of the skin contact surface of said RF applicator.

12. The skin treatment device of claim 6, wherein said liquid dispenser defines a flow path extending through said massage manipulator so as to deliver the liquid via said at least one massage head.

13. The skin treatment device of claim 12, wherein said massage head includes a plurality of spherical elements deployed to provide rolling engagement with the skin surface, and wherein said flow path delivers the liquid to a surface of at least one of said spherical elements for rolling application to the skin surface.

14. A skin treatment device comprising:
(a) a housing;
(b) an RF treatment arrangement deployed at least partially within said housing, the RF treatment arrangement comprising:
(i) an RF applicator terminating in a skin contact surface through which RF energy is delivered into the skin, and
(ii) an RF energy source capable of directing an RF power signal to said applicator; and
(c) a liquid dispenser deployed at least partially within said housing and configured to deliver a liquid to a region of skin underlying said RF applicator.

15. The skin treatment device of claim 14, wherein said liquid dispenser defines a flow path in thermal contact with at least part of said RF applicator.

16. The skin treatment device of claim 15, further comprising a cooling arrangement deployed within said housing and configured to cool the liquid, thereby cooling said RF applicator.

17. The skin treatment device of claim 14, wherein said liquid dispenser defines a flow path passing through at least part of said RF applicator.

18. The skin treatment device of claim 17, wherein said flow path terminates at a rolling ball liquid applicator formed as part of said RF applicator so as to provide at least part of the skin contact surface of said RF applicator.

19. The skin treatment device of claim 14, further comprising a mechanical massage arrangement comprising:
(a) a massage manipulator comprising at least one massage head, said massage manipulator defining a skin contact region, and
(b) a motor, mechanically linked in driving relation to said at least one massage head so as to displace said at least one massage head relative to a skin surface,
wherein said skin contact region substantially encircles said RF applicator such that, when the device is brought in contact with the skin and said RF treatment arrangement and said mechanical massage arrangement are actuated, mechanical massage is performed on a region of skin adjacent to, or overlapping with, a region treated by the RF energy.

20. The skin treatment device of claim 19, wherein said at least one massage head is an annular massage head deployed so as to encircle said RF applicator.

21. The skin treatment device of claim 20, wherein said annular massage head includes a plurality of spherical elements deployed to provide rolling engagement with the skin surface.

22. The skin treatment device of claim 21, wherein said liquid dispenser defines a flow path extending through said massage manipulator so as to deliver the liquid to a surface of at least one of said spherical elements for rolling application to the skin surface.

23. The skin treatment device of claim 20, wherein said annular massage head is rotatably mounted so as to rotate about an axis, and wherein said axis substantially coincides with a central axis of said RF applicator.

* * * * *